(12) United States Patent
Close et al.

(10) Patent No.: US 6,758,835 B2
(45) Date of Patent: Jul. 6, 2004

(54) DISPOSABLE NEEDLE ASSEMBLY HAVING SENSORS FORMED THEREIN PERMITTING THE SIMULTANEOUS DRAWING AND ADMINISTERING OF FLUIDS AND METHOD OF FORMING THE SAME

(75) Inventors: Benjamin W. Close, Aurora, IL (US); Thomas A. Hall, III, Chicago, IL (US)

(73) Assignee: MedTG, LLC, Naperville, IL (US)

( * ) Notice: Subject to any disclaimer, the term of this patent is extended or adjusted under 35 U.S.C. 154(b) by 65 days.

(21) Appl. No.: 10/137,186

(22) Filed: May 1, 2002

(65) Prior Publication Data

US 2003/0208154 A1 Nov. 6, 2003

(51) Int. Cl.[7] ............................. A61M 5/32; A61B 5/00
(52) U.S. Cl. .......................... 604/272; 600/327
(58) Field of Search .............................. 604/93.01, 264, 604/272; 600/310, 322, 323, 324, 325, 326, 327, 328, 342, 372, 373, 381, 581, 583

(56) References Cited

U.S. PATENT DOCUMENTS

| | | | |
|---|---|---|---|
| 3,490,441 A | 1/1970 | Curtis | |
| 3,610,226 A | 10/1971 | Albisser | |
| 3,841,307 A | 10/1974 | Friedell | |
| 3,958,562 A | 5/1976 | Hakim et al. | |
| 3,983,864 A | 10/1976 | Sielaff et al. | |
| 4,098,275 A | 7/1978 | Consalvo | |
| 4,160,448 A | 7/1979 | Jackson | |
| 4,665,927 A | 5/1987 | Daily | |
| 5,193,545 A | 3/1993 | Marsoner et al. | |
| 5,250,066 A | 10/1993 | Lambert | |
| 5,290,246 A | 3/1994 | Yamamoto et al. | |
| 5,312,361 A | 5/1994 | Zadini et al. | |
| 5,364,374 A | 11/1994 | Morrison et al. | |
| 5,374,245 A | 12/1994 | Mahurkar | |
| 5,378,230 A | 1/1995 | Mahurkar | |
| 5,395,319 A | 3/1995 | Hirsch et al. | |
| 5,451,206 A | 9/1995 | Young | |
| 5,568,806 A | 10/1996 | Cheney, II et al. | |
| 5,607,401 A | 3/1997 | Humphrey | |
| 5,637,399 A | 6/1997 | Yoshikawa et al. | |
| 5,876,366 A | 3/1999 | Dykstra et al. | |
| 5,891,105 A | 4/1999 | Mahurkar | |
| 5,951,521 A | * 9/1999 | Mastrototaro et al. | ...... 604/174 |
| 5,954,701 A | 9/1999 | Matalon | |
| 6,032,059 A | 2/2000 | Henning et al. | |
| 6,146,354 A | 11/2000 | Beil | |
| 6,221,058 B1 | 4/2001 | Kao et al. | |
| 6,228,864 B1 | 5/2001 | Smith et al. | |
| 6,245,079 B1 | 6/2001 | Nobles et al. | |
| 2001/0001125 A1 | 5/2001 | Schulman et al. | |
| 2001/0003991 A1 | 6/2001 | Sato et al. | |
| 2001/0007932 A1 | 7/2001 | Kamen et al. | |
| 2001/0009994 A1 | 7/2001 | Small et al. | |
| 2001/0016715 A1 | 8/2001 | Mayer | |
| 2001/0019019 A1 | 9/2001 | Nordman et al. | |
| 2001/0020591 A1 | 9/2001 | Hasegawa et al. | |
| 2001/0021429 A1 | 9/2001 | Nizuka et al. | |
| 2001/0025157 A1 | 9/2001 | Kriesell | |

* cited by examiner

Primary Examiner—Brian L. Casler
Assistant Examiner—Mark K Han
(74) Attorney, Agent, or Firm—Pillsbury Winthrop LLP

(57) ABSTRACT

A micro-injection molded disposable needle assembly having more than one passageway formed therein to permit the simultaneous drawing and administering of fluids through separate passageways is disclosed. The micro-injection molded disposable assembly includes one or more sensors disposed therein for measuring and monitoring one or more desired body or surrounding environmental conditions. A method of forming the disposable needle from an elastomeric material using micro-injection molding is also disclosed.

23 Claims, 13 Drawing Sheets

DISPOSABLE NEEDLE ASSEMBLY HAVING SENSORS FORMED THEREIN PERMITTING THE SIMULTANEOUS DRAWING AND ADMINISTERING OF FLUIDS AND METHOD OF FORMING THE SAME

BACKGROUND OF THE INVENTION

1. Field of the Invention

The present invention relates to a disposable needle assembly. In particular, the present invention is directed to a micro-injection molded disposable needle assembly having more than one passageway formed therein to permit the simultaneous drawing and administering of fluids through separate passageways. The present invention is also directed to a micro-injection molded disposable assembly having one or more sensors disposed therein for measuring and monitoring one or more desired conditions. The present invention is also directed to a method of forming a disposable needle from an elastomeric material using micro-injection molding.

2. Description of Related Art

U.S. Pat. No. 3,610,226 to Albisser discloses a double lumen cannula instrument for the withdrawal of blood over a prolonged period of time. The instrument includes an inner lumen for withdrawing blood and an outer lumen for introducing an anticoagulent diluent. The relative locations of the openings for the inner and outer lumen permit the mixing of the diluent with the withdrawn blood.

U.S. Pat. No. 5,374,245 to Mahurkar discloses an extruded reinforced multiple-lumen catheter for use in medical applications where fluids must flow simultaneously to and from a patient. Blood is withdrawn for a medical procedure (e.g. dialysis) from the patient through one passageway and returned to the patient through another passageway spaced from the first passageway.

U.S. Pat. No. 5,607,401 to Humphrey discloses augmented polymeric hypodermic needles and lancets. The polymeric needles and lancets are stiffened by augmenting means, which includes a slideable guard or foam insert so that they are able to pierce the skin. Without the augmenting means, it is not possible for the polymeric hypodermic lancet to pierce the skin.

U.S. Pat. No. 5,637,399 to Yoshikawa et al. discloses an extruded synthetic resin needle that is reinforced with combustible fibers. The needle provides a single path administering or withdrawing fluids from a patient.

The prior art described above does not provide for a needle assembly that is capable of prolonged insertion in the patient for both the simultaneous administering of intravenous fluids and the withdrawal of blood without mixing the intravenous fluid with the withdrawn blood. Furthermore, these needle assemblies do not permit the monitoring of the patient without the further insertion of additional needle assemblies or sensors into the patient.

Various devices for internally monitoring a patient are known. U.S. Pat. No. 3,490,441 to Curtis discloses an intra-arterial blood pressure transducer, which includes a needle that is inserted into a blood vessel. The patient's blood pressure is measured by measuring the deflection of a sheath surrounding the needle. U.S. Pat. No. 4,665,927 discloses a flexible probe formed from a flexible plastic for sensing and measuring temperature. The probe may take the form of a needle that is inserted into the patient. U.S. Pat. No. 5,568,806 to Cheney et al. discloses a transcutaneous sensor insertion set. The insertion set includes a needle assembly having a sensor assembly for insertion into a patient. Upon insertion, the needle assembly may be withdrawn leaving the sensor assembly in place for monitoring the patient. None of these devices permit the simultaneous insertion and/or withdrawal of fluids while monitoring the patient.

U.S. Pat. No. 6,032,059 to Henning et al. discloses a fluid sampling device having a needle assembly for sampling of blood and measuring an analyte of interest within the blood. The device includes an analysis device that determines the required amount of drug to be injected in response to the measured analyte without removal of the device from the patient's body. In operation, the needle assembly is inserted into a blood vessel of the patient. The blood then flows into the needle to contact the sensor assembly. The blood is analyzed. In response to the analysis, a drug dosage is automatically administered through needle assembly. Although U.S. Pat. No. 6,032,059 discloses a needle assembly connected to a sensor assembly, it does not disclose a needle assembly that permits the simultaneous insertion and withdrawal of fluids from the blood stream while performing a sensing operation. Furthermore, the needle assembly is not designed for prolonged insertion the patient.

OBJECTS OF THE INVENTION

It is an object of the present invention to provide a disposable needle assembly that is capable of drawing and administering fluids from a patient.

It is another object of the present invention to provide a disposable needle assembly that is formed from a non-bioreactive material, which permits implantation in a patient for extended periods of time. The present invention eliminates the need for multiple patient injections.

It is another object of the present invention to provide a disposable needle assembly that permits the simultaneous administering of intravenous fluids and the drawing of blood.

It is another object of the present invention to provide a disposable needle assembly that permits the simultaneous administering of intravenous fluids and the drawing of blood without contaminating the blood with the intravenous fluids.

It is yet another object of the present invention to provide a micro-injection molded disposable needle assembly having a plurality of passageways formed therein, wherein at least one of the passageways is provided to withdraw blood from the patient.

It is another object of the present invention to provide a micro-injection molded disposable needle assembly having a plurality of passageways formed therein, wherein at least one of the passageways is provided to administer an intravenous fluid to the patient.

It is another object of the present invention to provide a disposable needle assembly having a plurality of passageways formed therein, wherein at least one of the passageways is provided to withdraw blood from the patient.

It is another object of the present invention to provide a micro-injection molded disposable needle assembly having a plurality of passageways formed therein having a passageway for administering an intravenous fluid and a passageway to withdraw blood from the patient, wherein the passageway for withdrawing blood is capable of being flushed with intravenous fluid at predetermined times.

It is another object of the present invention to provide a disposable needle assembly having at least one sensor located therein for sensing one or more predetermined conditions including but not limited to, chemical agents in the blood stream, blood flow, pressure, and temperature.

It is another object of the present invention to provide a disposable needle assembly having at least one sensor containing at least one polarographic region for sensing chemical agents in the blood stream.

It is another object of the present invention to provide a disposable needle assembly having at least one electroconductive sensor for sensing at least chemical agents in the blood stream and temperature.

It is another object of the present invention to provide a disposable needle assembly having an optical sensor for sensing chemical agents and/or measuring intravenous pressure.

It is another object of the present invention to provide a disposable needle assembly having a flexible diaphragm for use in connection with the measurement of intravenous pressure.

It is another object of the present invention to provide a disposable needle assembly having a flexible diaphragm for use in connection with the measurement of a patient's pulse.

SUMMARY OF THE INVENTION

In response to the foregoing challenges, applicants have developed a needle assembly for use in connection with treating and monitoring a patient. The needle assembly is capable of administering fluids to the patient and also drawing fluids from the patient. The needle is preferably formed by micro-injection molding and is disposable.

The needle assembly includes an elongated needle shaft having a first end and a second end. The needle assembly includes an insertion tip located at a first end of the elongated needle shaft to facilitate insertion of the needle assembly into a vessel of the patient. The insertion tip is preferably integrally formed with the elongated needle shaft.

The needle assembly preferably includes at least one fluid drawing passageway formed in the elongated needle shaft for withdrawing fluid from the patient. Each fluid drawing passageway extends from the second end of the elongated needle shaft to a fluid drawing opening in the elongated needle shaft. The fluid (e.g., blood) within the vessel is withdrawn through the fluid drawing passageway. The drawn fluid may be remotely tested. It is also contemplated that the withdrawn fluid can be medically treated and returned to the vessel.

The needle assembly also preferably includes at least one fluid supply passageway formed in the elongated needle shaft for supplying fluid to the patient. Like the fluid drawing passageway, each fluid supply passageway extends from the second end of the elongated needle shaft to a fluid supply opening in the elongated needle shaft. The fluid introduced into the vessel through the fluid supply passageway may be an intravenous fluid containing nutrients and/or medicaments. It is also contemplated that the fluid supply passageway may return processed blood or plasma to the vessel.

In accordance with the present invention, the fluid supply opening and the fluid drawing opening are spaced from each other along the length of the elongated needle shaft. The spacing of these openings prevents the mixing of the fluid introduced through the fluid supply opening with the fluid removed from the vessel through the fluid drawing opening. It contemplated that one of the openings is located adjacent the insertion tip, while the other of the openings is spaced from the insertion tip.

The needle assembly preferably includes at least one sensor assembly disposed within the elongated needle shaft. The at least one sensor assembly senses at least one predetermined condition of the patient. The at least one sensor assembly may gather the necessary information for the performance of routine lab tests. It is contemplated that the sensor assemblies may be used in connection with Chem 21 testing, and complete blood counts (CBC testing). It is also contemplated that the sensor assemblies may be used in connection with the measurement of alcohol, sodium, potassium, and/or magnesium levels in the bloodstream. The sensor assemblies may also be used in connection with the measurement of internal and external pressures in the venous environment. Furthermore, sensor assemblies may be used to sense and measure body temperature and blood flow. This listing of potential tests and measurement of patient conditions is by no means intended to be exhaustive; rather, numerous other tests and procedures are often performed in connection with the injection of a needle in the patient are considered to be well within the scope of the present invention.

The sensor assembly is preferably disposed within the elongated needle shaft within a sensor passageway formed therein. A sensor is located within the passageway. Numerous sensors are considered to be well within the scope of the present invention including but not limited to optical sensors, temperature sensors, acoustic sensors, pressure sensors (e.g., flexible diaphragms), electrical sensors and chemical sensors. The optical sensor for providing real time visual inspection of the vessel and the blood flow therein. Temperature sensors may be used to measure patient temperature and individual organ temperature. It is also contemplated that the sensor may comprise an electro or chemical sensors. The elongated needle shaft preferably includes at least one recess formed in the outer surface of the shaft. The recesses expose portions of the sensors. It is also contemplated that the above-described sensors may be linked to both visual and audible indicators. For example, an audible indication of blood pressure may be provided in to response to measurement by the sensors.

The elongated needle shaft of the staged needle is preferably formed from an elastomeric material by micro-injection molding. In order to minimize discomfort to the patient, the elastomeric material has a durometer that is slightly greater than the durometer of flesh. The matching of durometer will reduce the uncomfortable irritation of the target vein. This minimization of discomfort permits the needle assembly to be an inserted position in the patient for longer periods of time, which reduces the number of necessary injections. Because this durometer selection, a molded removable core pin used is in connection with the insertion of the needle assembly into vein. The core pin temporarily increases the stability of the needle assembly during the insertion operation. Upon insertion, the core pin is extracted and disposed of, leaving the needle in place.

In accordance with the present invention, the elongated needle shaft is connected to a connector assembly. The connector assembly is secured to the second end of the elongated needle shaft. The connector assembly includes at least one inlet port operatively connected to the at least one fluid supply passageway and at least one outlet port operatively connected to the at least one fluid drawing passageway. Furthermore, the necessary connections for the sensor assemblies are located within the connector assembly. This permits the needle assembly to be connected to a control unit or a monitoring device. The connector assembly may be connected to an attachment assembly for releasably securing the needle assembly to the patient. The attachment assembly may be in the form of the arm band or strap used to secure the needle in place on the patient. The needle assembly is preferably disposed at angle with respect to the attachment assembly.

The present invention is also directed to a method of forming a disposable needle assembly, discussed above. The method includes forming the elongated needle shaft by micro-injection molding. The method further includes forming the connector assembly and securing the connector assembly to the elongated needle shaft. The elongated needle shaft is formed around the at least one sensor assembly. The method further includes forming a removable core pin.

A method of treating a patient is also contemplated in accordance with the present invention. The method includes inserting a disposable needle assembly into a vessel of the patient. The insertion of the disposable needle assembly may also include the insertion of a molded core insert. The moldable core insert is located within one of the passageways of the elongated needle shaft. The core is preferably located within the passageway that extends from the second end to the first end of the shaft adjacent the insertion tip. The moldable core increases the stability of the needle assembly during the insertion process. Upon insertion of the needle assembly within the vessel, the moldable core insert is removed.

The method further includes periodically withdrawing a sample of blood from the patient through a first passageway formed in the elongated needle shaft. The removable of a sample of blood permits the analysis of the blood. Furthermore, a supply an intravenous fluid to the patient may be fed through a second passageway formed in the elongated needle shaft. While this removal of blood and supply of fluid is being performed, the patient can also be monitored through at least one sensor assembly located within the needle assembly. This method is especially advantageous when, for example, a patient is being transferred by emergency vehicle to an emergency room. The paramedics can begin administering necessary IV fluids while monitoring the patient with the insertion of a single needle assembly in the patient. Furthermore, many of the testing operations, discussed above, can be begun or completed before the patient arrives at the emergency room.

Once the testing data is readable, it will be made available to paramedics through a display panel that may be operatively connected to the needle assembly. It is also contemplated that the testing data may be wirelessly transmitted in advance to medical personnel either from an ambulance or critical care unit to a hospital to inform medical staff of the patient's current physical conditions through different media options.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
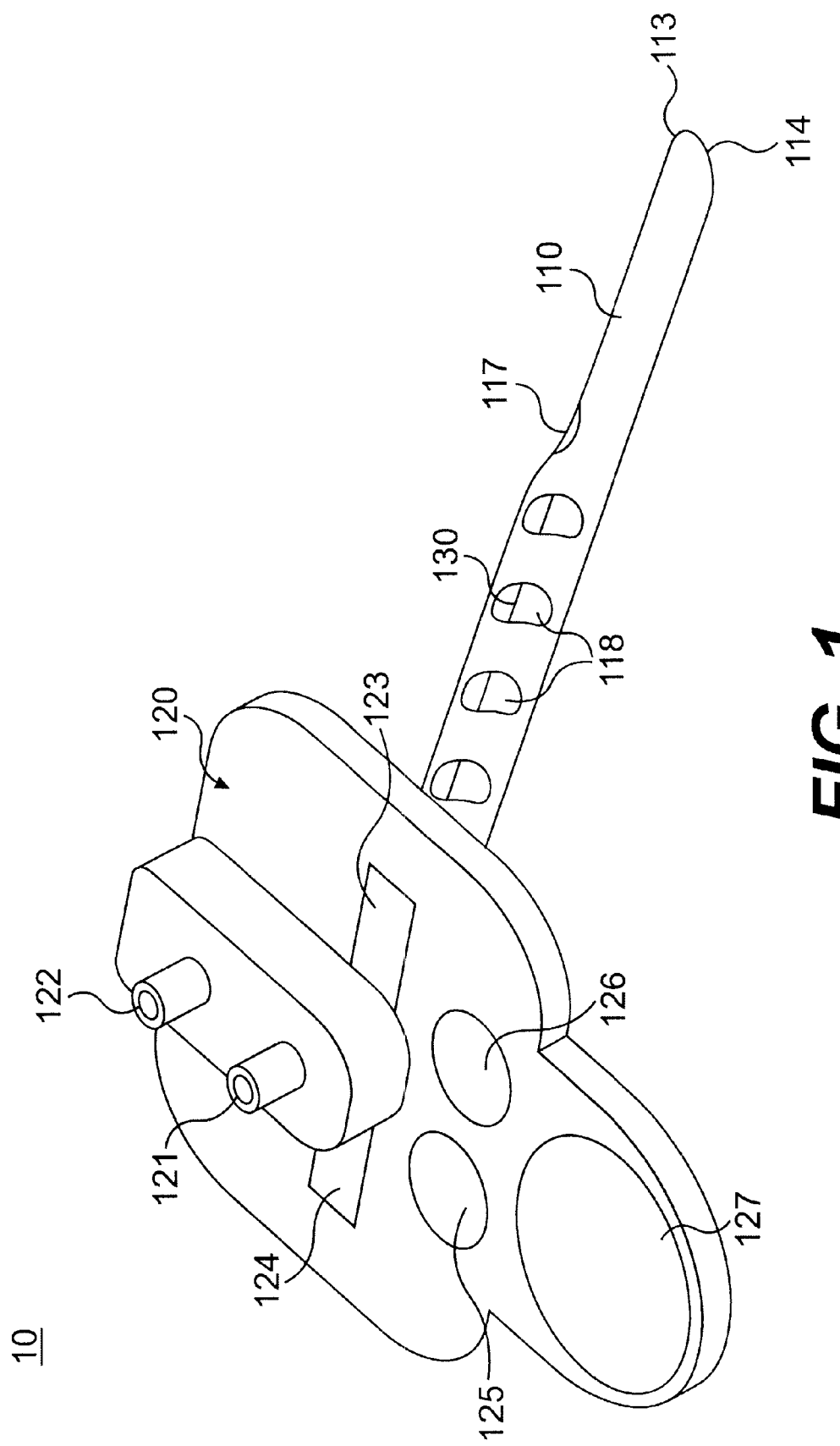
FIG. 1 is a schematic view of a disposable needle assembly in accordance with the present invention.

A disposable needle assembly 10 in accordance with the present invention will be described in connection with FIGS.

1–5. The principle behind the disposable needle assembly 10 is a staged needle having an elongated shaft, which is configured in such a way as to allow uncontaminated blood draws while administering IV fluids.

The disposable needle assembly 10 includes an elongated staged needle 110. The staged needle 110 is preferably molded from an elastomertic material whose durometer is chosen just above that of flesh to minimize discomfort to the patient. This minimization of discomfort permits the needle assembly 10 to be an inserted position in the patient for longer periods of time, which reduces the number of necessary injections. Suitable elastomeric materials for the construction of the staged needle 110 include polyesters, polyester polypropylene blends, latex, silicone rubber and thermoplastic elastomers. The present invention, however, is not limited to these elastomeric materials; rather, other elastomeric materials are contemplated provided such materials have durometers similar to flesh and will not irritate skin in response to prolonged exposure.

The elongated staged needle 110 is sized to permit easy insertion into the vein or vessel of the patient. The elongated staged needle 110 is also sized to remain inserted within the vessel for extended periods of time with minimal discomfort. It is contemplated that the elongated needle 110 a length between 2 cm to 4 cm with diameters from 2 mm to 4 mm. The present invention, however, is not limited to these dimensions. Smaller dimensions are contemplated for elongated needles used for neonatal applications. Furthermore, larger dimensions are contemplated for elongated needles used for animal applications.

The staged needle 110 will now be described in greater detail. The staged needle 110 includes first and second passageways 111 and 112, which are integrally formed therein. The staged needle 110 has an insertion tip 113 formed in one end thereof. An opposite end of the needle 110 is connected to a connector assembly 120, described in greater detail below. The insertion tip 113 is shaped to facilitate insertion into the desired vein or vessel of the patient.

Figure 3:
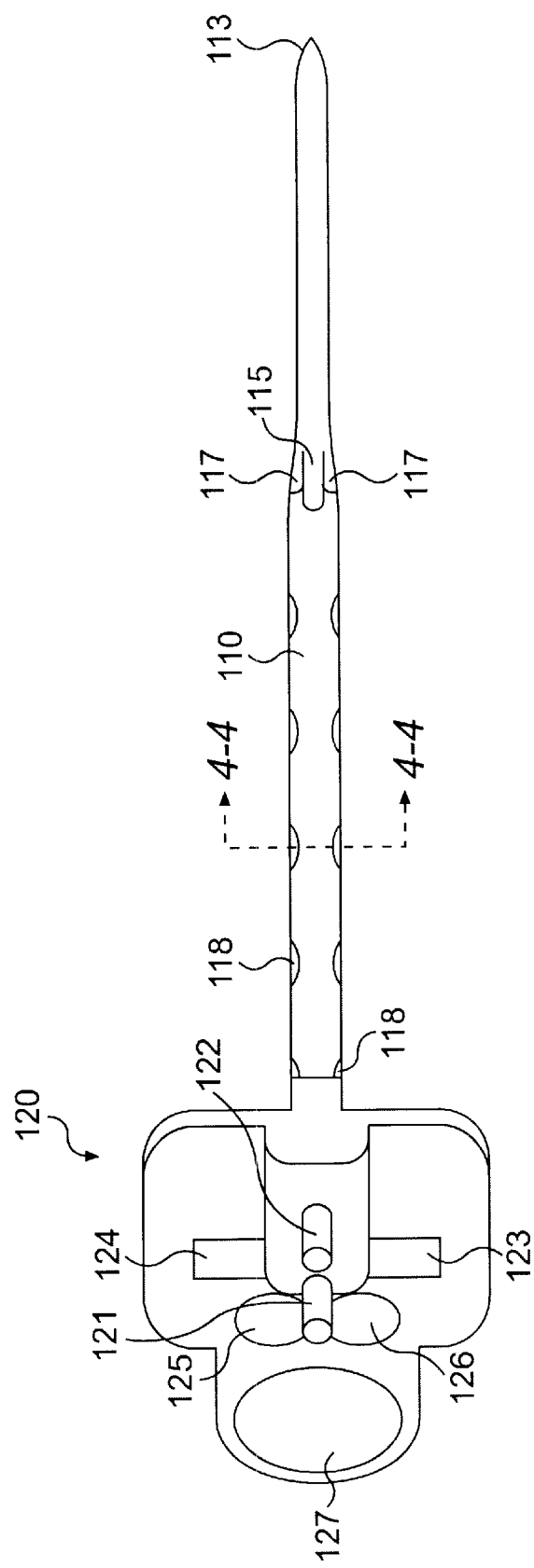
FIG. 3 is a top view of the disposable needle assembly of FIG. 1.
Figure 4:
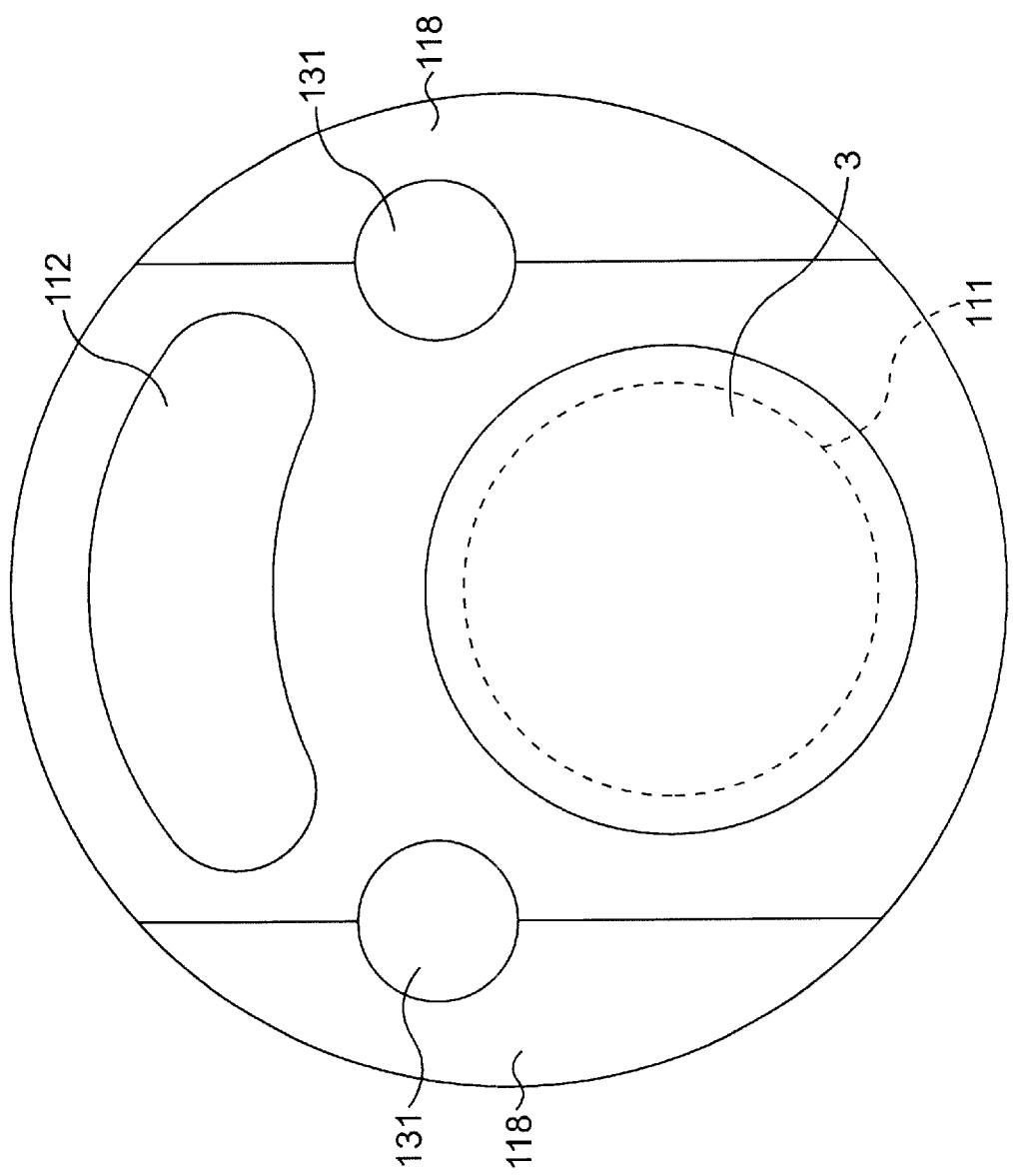
FIG. 4 is a cross sectional view along section lines 4—4 of the disposable needle assembly of FIG. 3.
Figure 5:
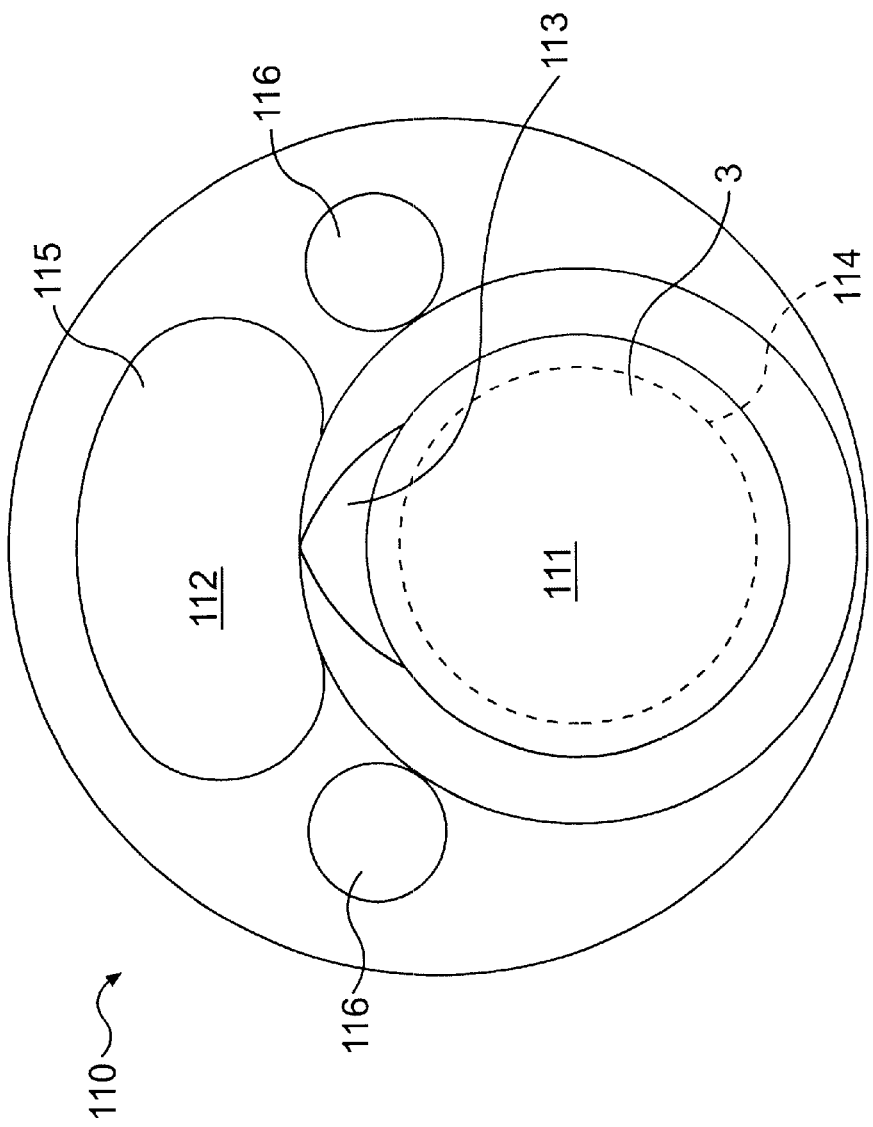
FIG. 5 is an end view of the disposable needle assembly of FIG. 1.

The first passageway or conduit 111 extends through the needle 110 from the connector assembly 120 to an opening 114 adjacent the insertion tip 113, as seen in FIG. 3. The first conduit 111 is provided to introduce fluids (e.g., intravenous fluid) into the vessel. The present invention, however, is not limited to a single conduit 111 for the purpose of introducing fluids into the vessel; rather, it is contemplated that one or more conduits may be formed in the staged needle 110 for the purpose of supplying fluids to the patient through the vessel. A removable core pin 3, shown in phantom in FIGS. 4 and 5, is located in the conduit 111 during the insertion operation to strengthen the tip of the needle assembly 10 to facilitate insertion. The present invention is not limited to the core pin 3 being located within the conduit 111; rather, it is contemplated that the core pin 3 may be located within the conduit 112 or other suitable passageway formed in the needle assembly 10. It is further contemplated that the core pin 3 may extend through both the conduit 111 and 112. Upon insertion of the needle assembly 10 in the vessel, the core pin 3 is removed The second passageway or conduit 112 extends through the needle 110 from the connector assembly 120 to an opening 115 spaced from the insertion tip 113, as seen in FIG. 3. The second conduit 112 is provided to draw a sample of fluid (e.g. blood) from the vessel. The openings 114 and 115 are spaced along the axis of the elongated shaft of the staged needle 110. The differential location of the openings 114 and 115 permits uncontaminated blood draws while simultaneously administering IV fluids.

Although the first conduit 111 has been described in connection with the introduction of fluids into the vessel, the present invention is not so limited. It is contemplated that the first conduit 111 may be used to withdraw fluids from the vessel or bloodstream. Furthermore, it is also contemplated that the second conduit 112 may be used in connection with the supply to fluids to the vessel. It is still further contemplated that both the first and second conduits 111 and 112 may be used in connection with the introduction of fluids (e.g., nutrients and medicaments) into the vessel, as described in greater detail below.

The elongated staged needle 110 is also provided with one or more sensor assemblies. In accordance with the present invention, these sensor assemblies are integrated into the staged needle 110 and include multiple arrays of external and internal sensors 130. Various sensors are considered to be well within the scope of the present invention including but not limited to optically based sensors, acoustic sensors, pressure based sensors, chemical based sensors, electrical based sensors and temperature based sensors.

Figure 2:
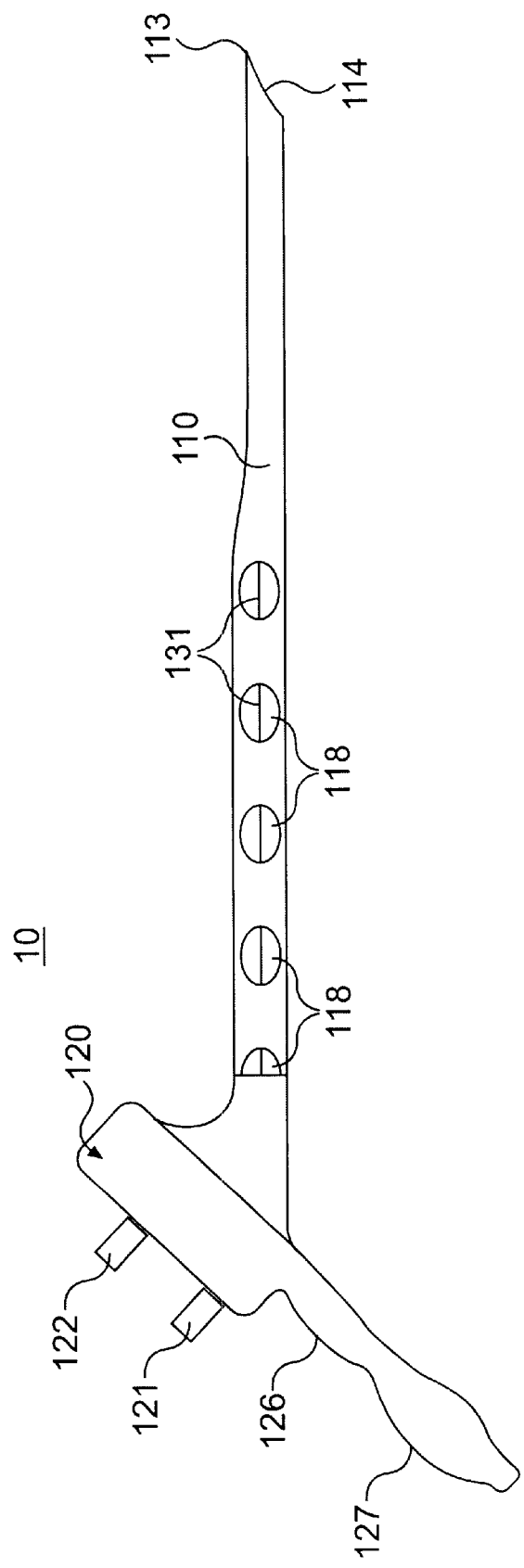
FIG. 2 is a side view of the disposable needle assembly of FIG. 1.

The sensors 130 are located in one or more sensor channels or passageways 116 are formed in the staged needle 110, as shown in FIGS. 1, 4 and 5. The passageways 116 extend generally parallel to the conduits 111 and 112 and terminate in a sensor access orifice 117. The present invention, however, is not limited to passageways 116 that are generally parallel; rather, it is contemplated that the sensor channels may extend in a spiral or zig-zag pattern. As shown in FIGS. 2 and 5, the orifices 117 are located adjacent the opening 115. With this arrangement, it is possible to test and monitor the blood as it enters the passageway 112.

The staged needle 110 further includes one or more dimples or recesses 118 formed along the length of the needle 110, as shown in FIGS. 2–4. The recesses 118 provide sensory access to the sensors located within the passageways 116. The recesses 118 are molded on the needle shaft 110, in such a way as to prevent the collection of bodily fluid born agents (i.e. blood cells). A red blood cell is approximately 5 to 7 micrometers in diameter, a white blood cell approximately 10 micrometers. No protrusions or recesses 118 of sufficient size as to capture blood cells are allowed or cells can be damaged. The area about the sensor region is a continuous curved surface as to not capture and stagnate the blood and of ample size as to prevent shut off of the sensor from the blood flow if it comes in contact with the vein wall. The recesses 118 provide venous fluid contact with the sensor assemblies. A sensor assembly 130 is located in each of the passageways 116. The sensor assembly 130 may include an optical fiber, examples are described below, or an electrically conductive wire, examples are described below. The sensor assemblies 130 are molded into the staged needle 110 during the manufacture of the needle 110. The recesses 118 may be formed into the side of needle shaft 110. It is also contemplated that the outer surface of the needle shaft 110 may include one or more areas having an increased diameter (not shown), the areas between adjacent areas of increased diameter form the recesses 118.

Various types of electrical sensors are contemplated, including but not limited to capacitance based sensors, resistance based sensors, amperage based sensors and voltage based sensors. In a capacitance based electrical sensor, the variance in ambient pressure about the sensor will allow a set of parallel plates to vary in position thus changing the capacitance of the sensor. In a resistance based electrical sensor, the variance of a blood borne agent will chemically react with a sensing medium changing the resistance of the medium in such a way as to be able to measure and thus determine the concentration of the agent present. The same effect can be made through changing the resistance of a sensor element through the application of either temperature or pressure. In an amperage based electrical sensor, a blood borne agent will chemically react in the presence of a catalyst present in a sensing medium in such as way as to release valence electrons and thus create a current flow (amperage) in amplitude which is in function with the concentration of the agent present. In a voltage based electronic sensor, a blood borne agent reacts with differing materials present at the tips of the sensing wires thus creating a difference in potential and thus a voltage which can be monitored to determine the concentration of the agent.

Figure 6:
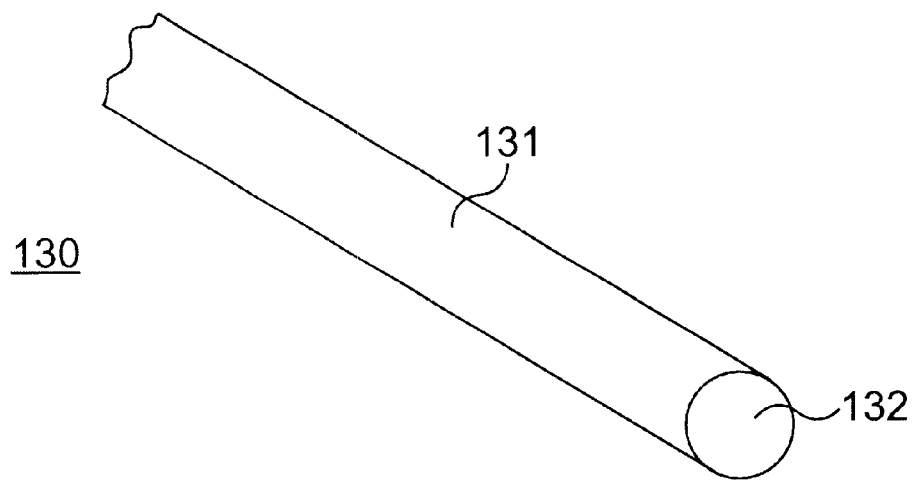
FIG. 6 is a schematic view of a sensor for use in the disposable needle assembly in accordance with the present invention.

It is contemplated that the needle assembly 10 may connected to a micro-injection molded spectrometer. The spectrometer is used for the color sensing of the polarographic type sensor region within the blood stream. A light source (e.g., white light) is focused down an optic fiber 131, extending through the staged needle 110 and reflected off of the chemically sensitive node 132, shown in FIG. 6, which may be provided in orifice 117. The node 132 is formed from a suitable material that is capable of changing color in response to the presence of a target chemical agent in the blood stream. The white light is reflected back as a particular color. The colored light is reflected off of a diffractive grating and is divided into individual wavelengths. The divided light is struck onto a detector array the pattern of increased and decreased intensities along a distance on the array corresponds to the color of the chemically sensitive node, which in turn corresponds to a density of the target agent in the solution.

Figure 7:
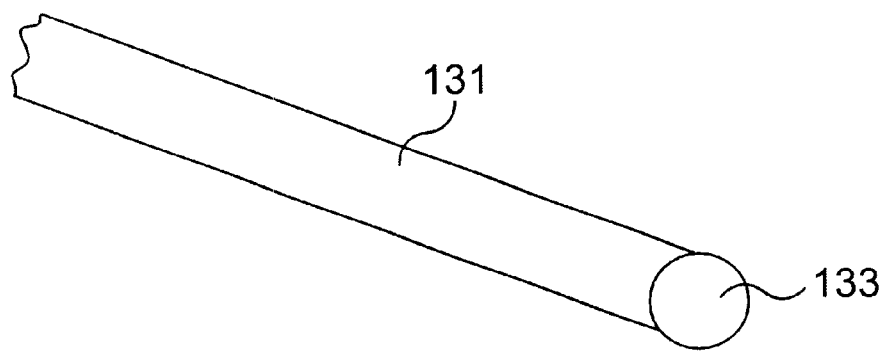
FIG. 7 is a schematic view of another sensor for use in the disposable needle assembly in accordance with the present invention.

It is also contemplated that the needle assembly 10 may be connected to a single component molded michelson interferometer, which is used to measure venous pressure and pulse rate. The interferometer includes a molded beam splitter element, an optic fiber 131 and a flexible diaphragm 133, shown in FIG. 7. From a lens element of the interferometer, a light beam is collimated and split into two beams. A first beam is directed to the detector array. A second beam is directed through the staged needle 110 through an optical fiber 131 having diaphragm 133 located at an end thereof. The beam is reflected off of the diaphragm 133 and reflected off of the beam splitter creating an interference pattern with the original beam. The diaphragm geometry is such that when the pressure in the blood stream increases the diaphragm 133 deflects inward shortening the distance the light reflects back. This change in length creates a change in interference pattern, which is easily monitored on the detector array.

The connector assembly 120 will now be described in greater detail. The connector assembly 120 is secured to the elongated staged needle 110. The connector assembly 120 includes a supply port 121 operatively connected to the first conduit 111. The supply port 121 includes a valve assembly 1211 formed therein. It is contemplated that the valve assembly 1211 may be manually or automatically operable to control the flow of fluid into the needle assembly 10. The connector assembly 120 further includes a draw port 122 operatively connected to the second conduit 112. The draw port 122 also includes a valve assembly 1221 formed therein. The valve assembly 1221 prevents the flow of fluid from the needle assembly 10 unless an extraction device 2 is connected to the draw port 122. The medical provider can withdraw a sample of blood through the port 122. When desired, fluid can also be supplied through the port 122.

Figure 8:
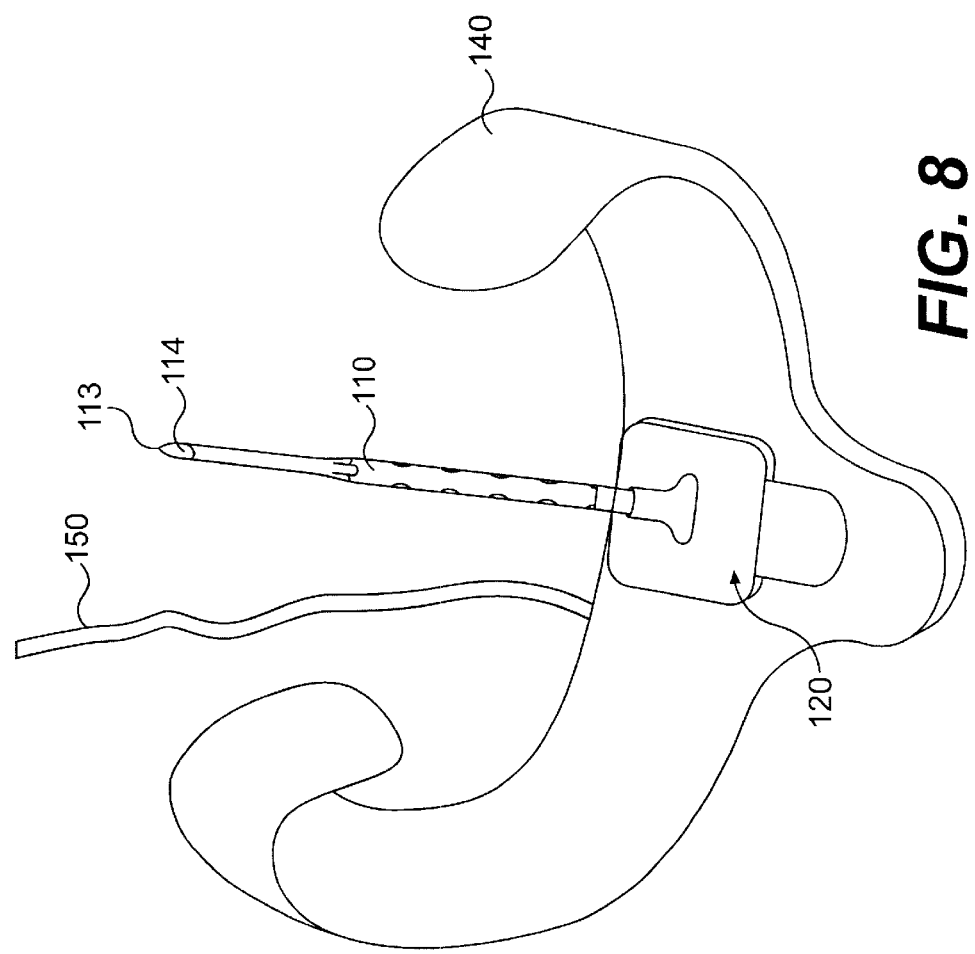
FIG. 8 is a bottom schematic view of the disposable needle assembly connected to an arm band for attachment to a patient in accordance with an embodiment of the present invention.
Figure 9:
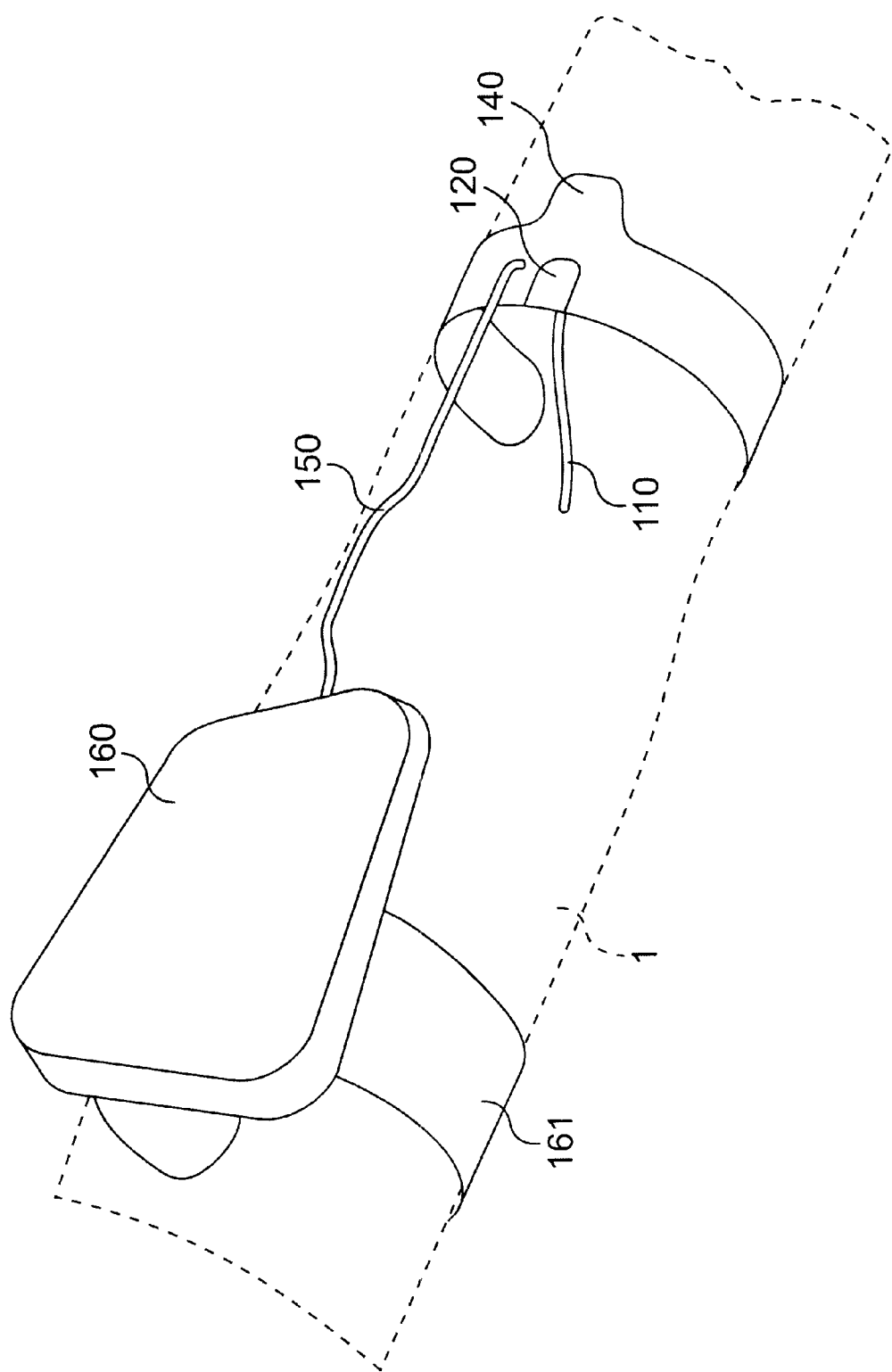
FIG. 9 is a schematic view of the disposable needle assembly connected to an arm band and operatively connected to a control unit.

The connector assembly 120 further includes sensor connector assemblies 123 and 124, which are operatively coupled to the sensor assemblies 130 provided in the staged needle 110. The sensor connector assemblies 123 and 124 link the sensor assemblies 130 in the staged needle 110 with sensor components and circuitry located within a mounting assembly 140. The mounting assembly 140 is preferably formed as an armband, as shown in FIGS. 8 and 9. The present invention, however, is not limited to an arm band construction; rather, various mounting devices including but not limited to belts, sleeves, hook and loop fastener assemblies and tape are considered to be well within the realm of the present invention.

The connector assembly 120 also includes a valve operating system for switching between operating modes (e.g., solely supplying fluid to simultaneously supplying fluid and drawing blood) and flushing the second conduit 112, when desired, as shown in FIGS. 13–17. The valve operating system is integrally formed in the connector assembly 120, as shown in FIG. 8. The valve operating system includes at least one selectively operable valve assembly 125 and 126 and a flushing reservoir 127. The valve assemblies 125 and 126 are preferably diaphragm valves. The present invention, however, is not limited solely to the use of such valves; rather, it is contemplated that other valves including but not limited to butterfly valves, knife valves and pinch valves may be used.

Figure 13:
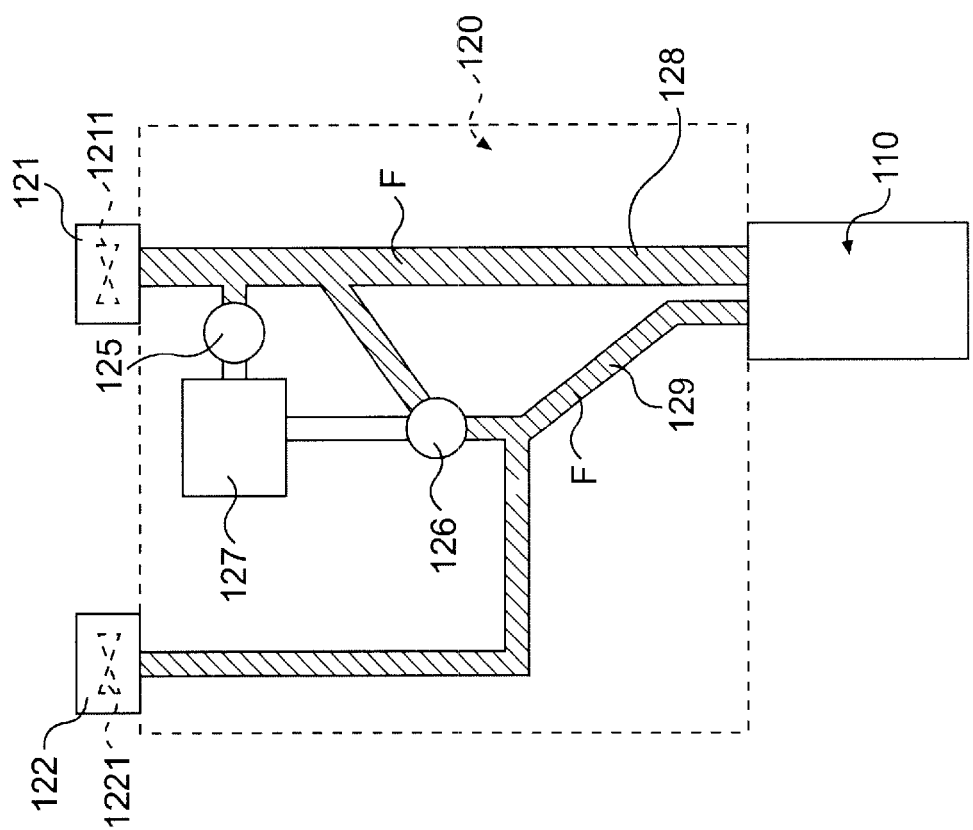
FIG. 13 is a schematic diagram illustrating the flow path of IV fluids within the connector assembly of the needle assembly in accordance with one embodiment of the present invention during administering of IV fluids.

In accordance with a first embodiment of the connector assembly 120 illustrated in FIGS. 13–17, when it is desirable to supply fluids to the patient through both conduits 111 and 112, the valve assemblies 1211 and 1221 are operated to permit the flow of fluid through the connector assembly 120 to both conduits 111 and 112, as shown in FIG. 13. The valve assembly 1211 is in an open position to permit the flow of fluid F through a first passageway 128 into the first conduit 111 of the staged needle 110. The first passageway 128 is operatively coupled to a second passageway 129 through the valve assembly 126. The second passageway 129 is operatively connected to the second conduit 112. When it is desired to supply fluids through both conduits 111 and 112, the valve assembly 1221 is in a closed position to prevent the flow of fluid out of port 122. The valve assembly 126 is in a first open position to permit the flow of fluid from the first passageway 128 into the second passageway 129, as shown in FIG. 13. With this arrangement, the IV fluid may be supplied to the patient through conduit 111 and 112. It is contemplated that the same fluid may flow through both conduits or that different fluids may flow through the different conduits. When is it desired to supply different fluids through the conduits 111 and 112, the valve assembly 126 remains in a closed position such that fluid from the first passageway 128 does not flow into the second passageway 129. The valve assembly 1221 is an open position to permit the flow of fluid through port 122 into the second passageway 129.

Figure 14:
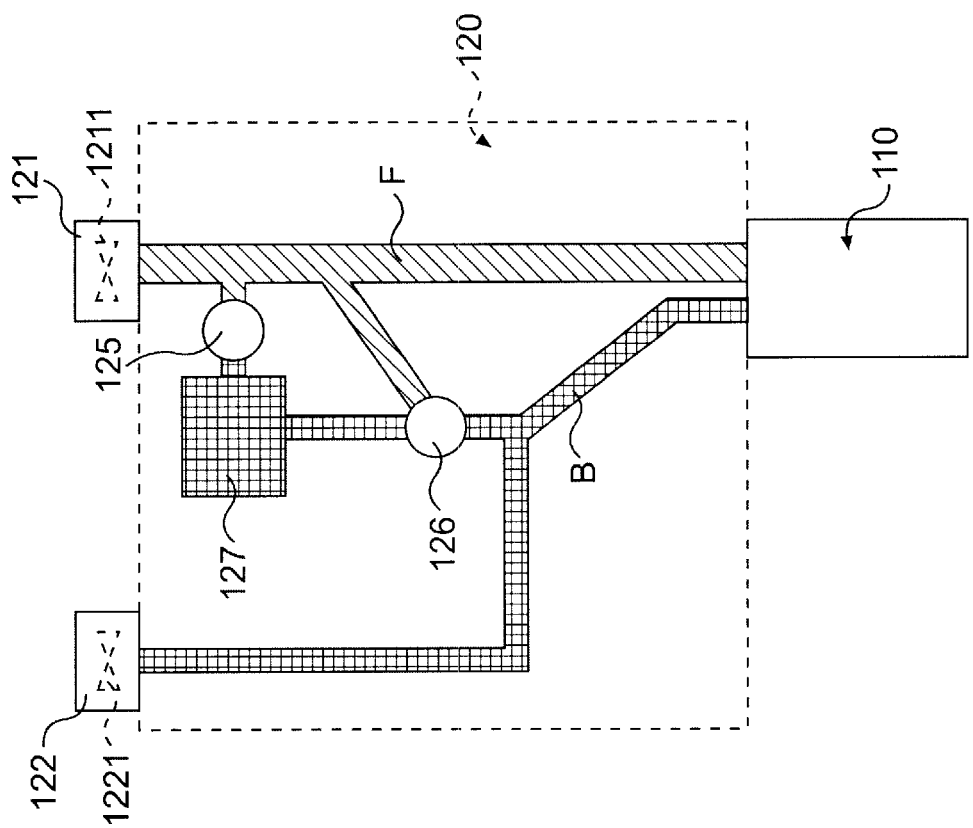
FIG. 14 is a schematic diagram illustrating the flow path of IV fluids and blood within the connector assembly of the needle assembly in accordance with one embodiment of the present invention during the initiation of a blood drawing operation.

When it is desired to draw blood B from the patient, the fluid contained in the conduit 112 and the second passageway 129 must be cleared to avoid contamination and mixing with the blood sample. To clear the conduit 112 and the second passageway 129, the valve assembly 126 is operated to a second operating position to cut of the supply of fluid from the first passageway 128. When in the second operating position, the valve assembly 126 opens a fluid pathway between the second passageway 129 and the flushing reservoir assembly 127, as shown in FIG. 14. Blood and any remaining fluids in the second passageway 129 is permitted to flow into the flushing reservoir 127.

Figure 15:
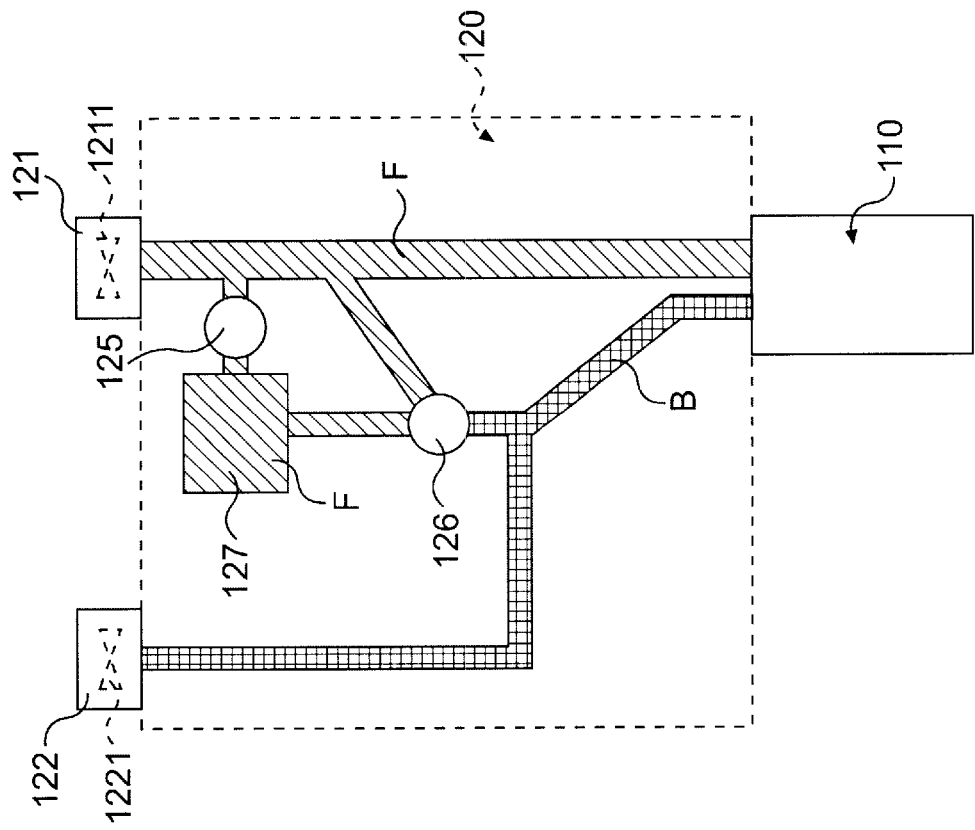
FIG. 15 is a schematic diagram illustrating the flow path of IV fluids and blood within the connector assembly of the needle assembly in accordance with one embodiment of the present invention during the withdrawal of a blood sample during the blood drawing operation.

Once the flushing reservoir assembly 127 is full, the valve assembly 126 is moved to a closed position, whereby fluid is not permitted to flow from the first passageway 128 or the flushing reservoir assembly 127 into the second passageway 129, as shown in FIG. 15. The flushing reservoir assembly 127 is of sufficient size to contain the mixture of blood and fluid such that uncontaminated blood remains in the second passageway 129. The extraction device 2 is then brought into contact with the port 122 and the valve assembly 1221 is opened to permit the withdrawal of the blood sample from the second passageway 120.

Figure 16:
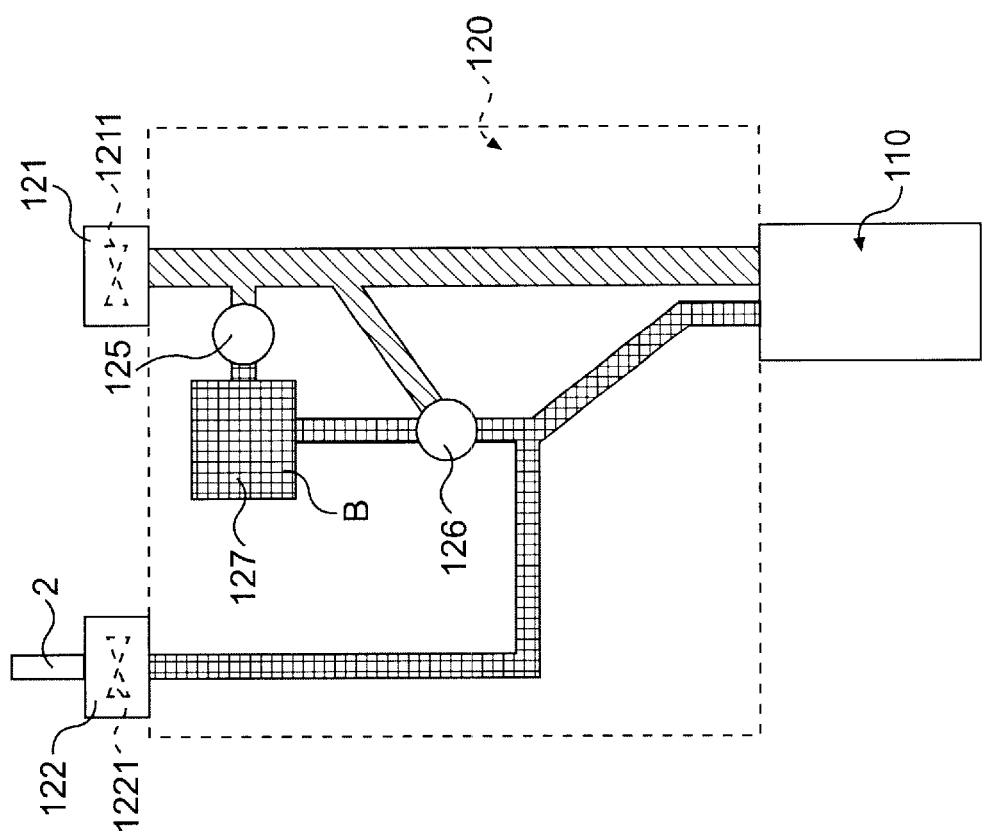
FIG. 16 is a schematic diagram illustrating the flow path of IV fluids and blood within the connector assembly of the needle assembly in accordance with one embodiment of the present invention after the withdrawal of a blood sample.
Figure 17:
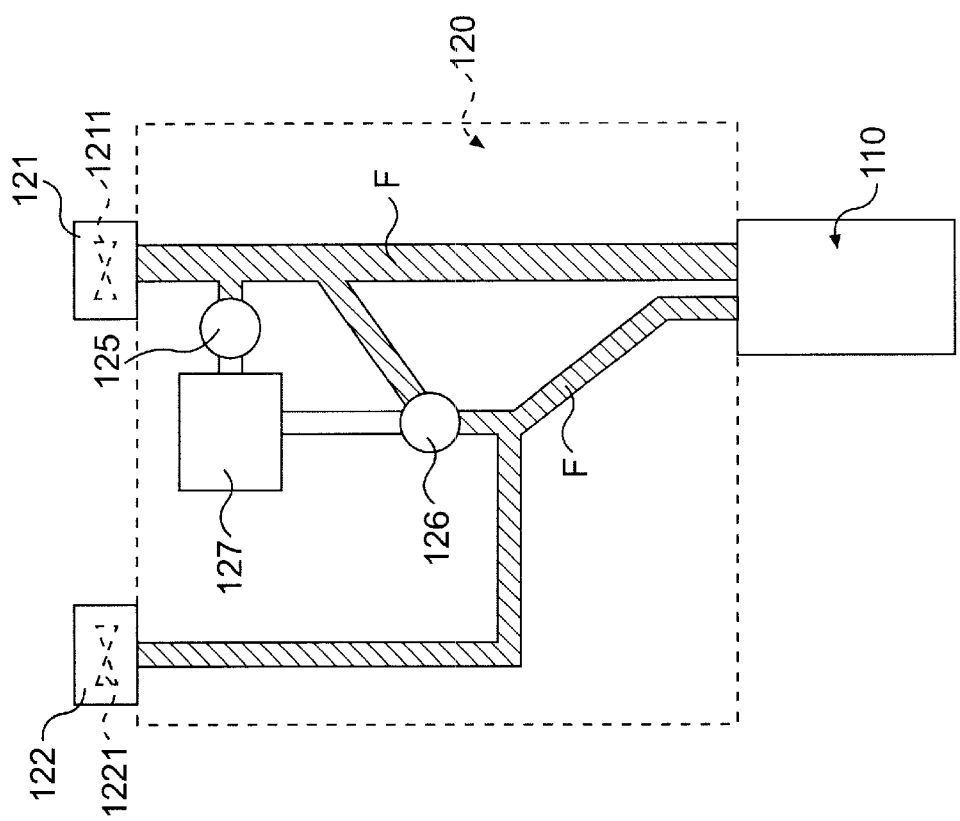
FIG. 17 is a schematic diagram illustrating the flow path of IV fluids and blood within the connector assembly of the needle assembly in accordance with one embodiment of the present invention at the completion of the blood drawing operation.

Once the blood sample has been withdrawn, the flow of fluid through the second passageway 129 can be reinstated. The valve assembly 126 is returned to the second operating position to permit the flow of the blood and fluid mixture in the reservoir assembly 127 into the second passageway 129. The valve assembly 125 is then operated to an open position to permit the flow of fluid from the first passageway 128 into the flushing reservoir assembly 127, as shown in FIG. 16. The fluid flows from the first passageway 128 through the flushing reservoir assembly 127 into the second passageway. After a sufficient amount of time so that the mixture of blood and fluid is removed from the flushing reservoir assembly 127, the valve assembly 126 is operated to a closed position to cut off the flow of fluid into the flushing reservoir assembly 127. The contents of the flushing reservoir assembly 127 then empty into the second passageway 128. Once the flushing reservoir assembly 127 is substantially empty, as shown in FIG. 17, the valve assembly 126 is switched to the first operating position such that fluid flows from the first passageway 128 through the valve assembly 126 into the second passageway 129.

Figure 18:
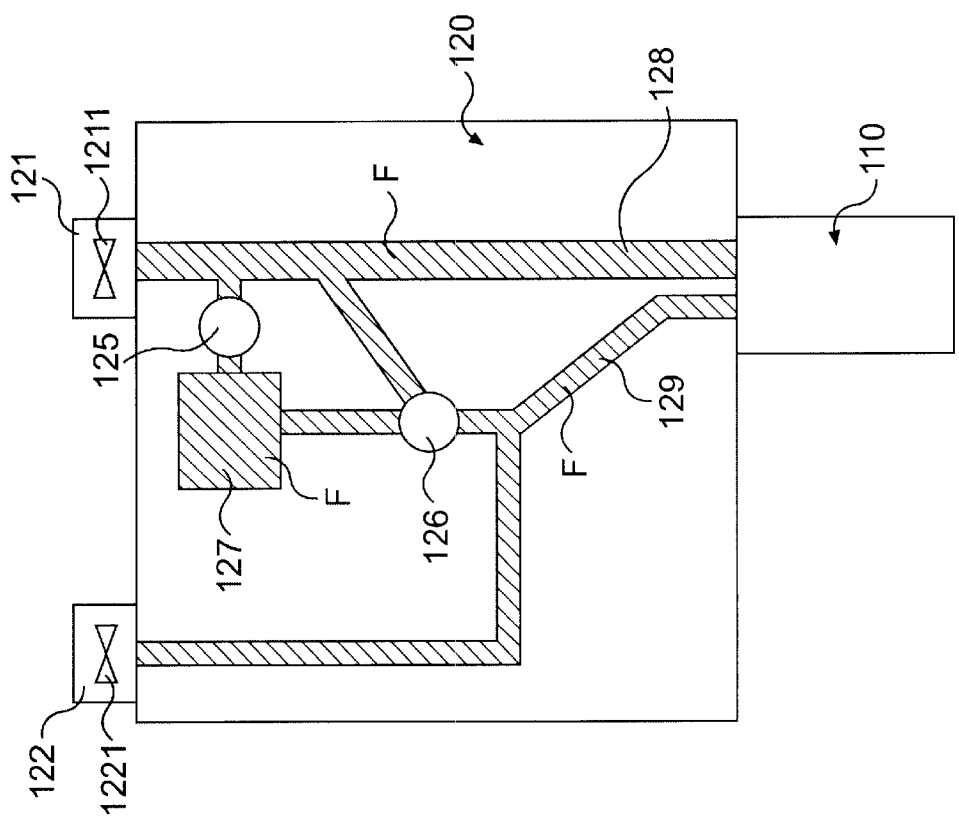
FIG. 18 is a schematic diagram illustrating the flow path of IV fluids within the connector assembly of the needle assembly in accordance with a preferred embodiment of the present invention.
Figure 20:
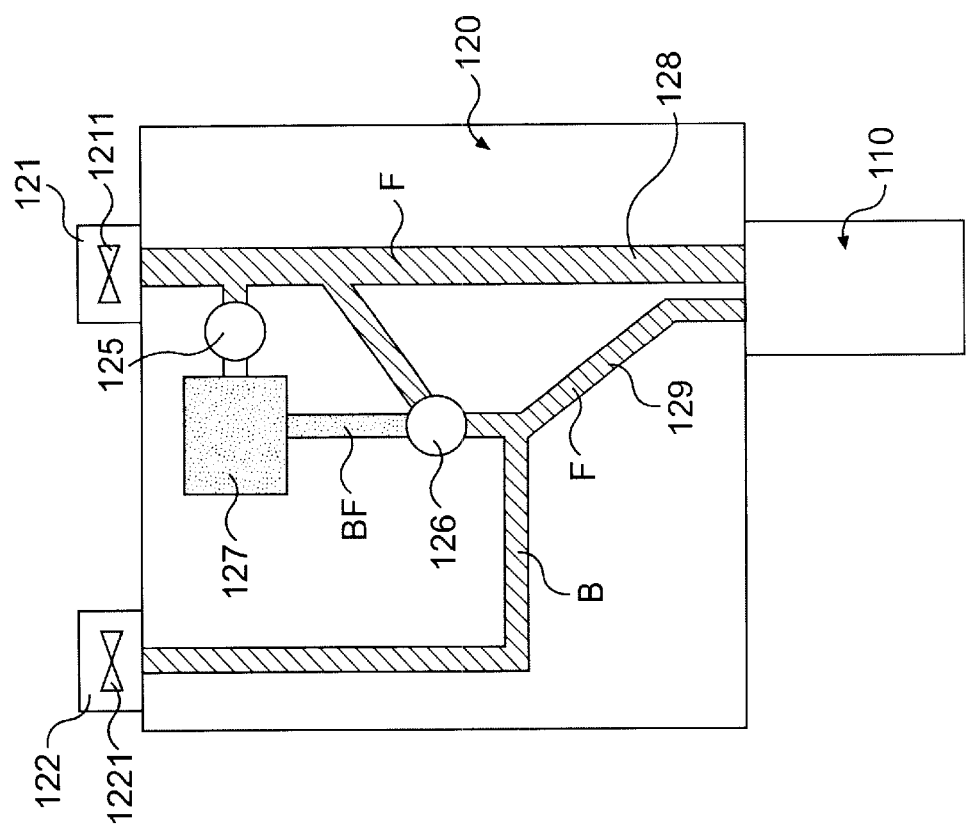
FIG. 20 is a schematic diagram illustrating the flow path of IV fluids and blood within the connector assembly of the needle assembly in accordance with a preferred embodiment of the present invention.
Figure 19:
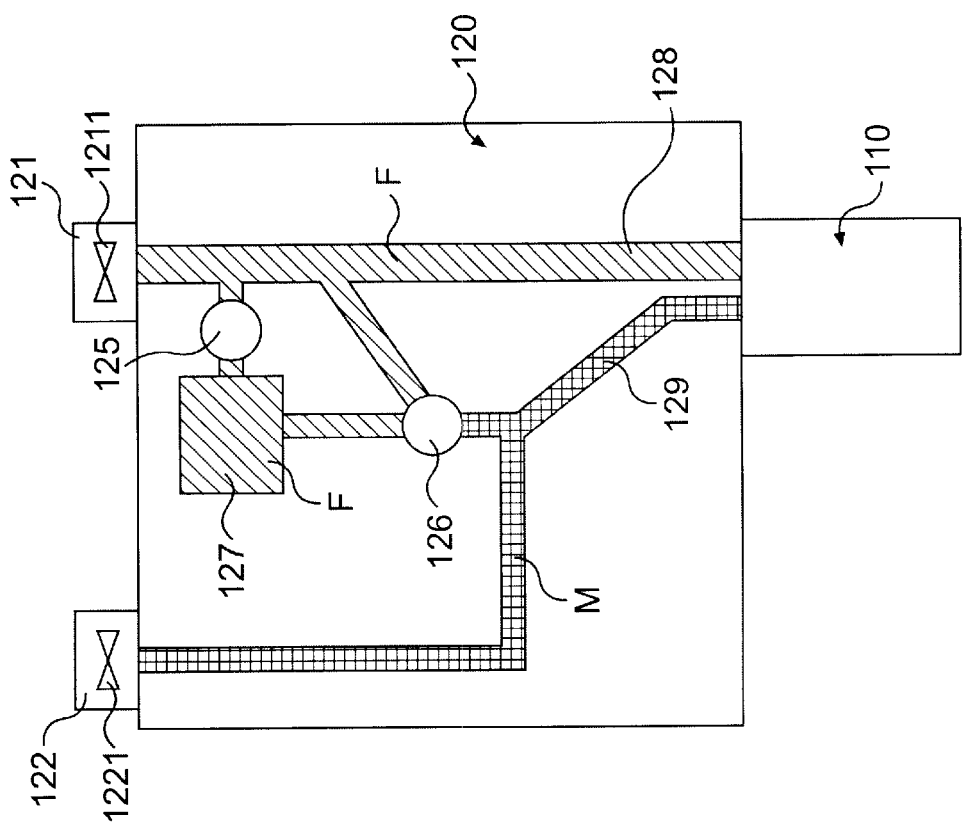
FIG. 19 is a schematic diagram illustrating the flow path of IV fluids and medication within the connector assembly of the needle assembly in accordance with the preferred embodiment of the present invention.

In accordance with a second preferred embodiment of the connector assembly 120 illustrated in FIGS. 18–20, when it is desirable to supply fluids to the patient through both conduits 111 and 112, the valve assemblies 1211 and 1221 are operated to permit the flow of fluid through the connector assembly 120 to both conduits 111 and 112, as shown in FIG. 18. The valve assembly 1211 is in an open position to permit the flow of fluid F through a first passageway 128 into the first conduit 111 of the staged needle 110. The first passageway 128 is operatively coupled to a second passageway 129 through the valve assembly 125. The second passageway 129 is operatively connected to the second conduit 112. When it is desired to supply fluids through both conduits 111 and 112, the valve assembly 1221 is in a closed position to prevent the flow of fluid out of port 122. The valve assemblies 125 and 126 are opened to permit the flow of fluid from the first passageway 128 into the second passageway 129, as shown in FIG. 18. With this arrangement, the IV fluid may be supplied to the patient through conduit 111 and 112. It is contemplated that the same fluid may flow through both conduits or that different fluids may flow through the different conduits. When is it desired to supply different fluids through the conduits 111 and 112, the valve assembly 126 remains in a closed position such that fluid from the first passageway 128 does not flow into the second passageway 129. The valve assembly 1221 is an open position to permit the flow of fluid through port 122 into the second passageway 129.

As shown in FIG. 19, when it is desired to draw blood B from the patient, the fluid contained in the conduit 112 and the second passageway 129 must be cleared to avoid contamination and mixing with the blood sample. To clear the conduit 112 and the second passageway 129, the valve assembly 125 is closed to cut of the supply of fluid from the first passageway 128. The flushing reservoir assembly 127 is evacuated by either compressing a flexible camber, shown in 1, or by actuating a plunger assembly to withdraw the fluid contained therein. When the flushing reservoir assembly 127 is evacuated, a mixture BF of fluid and blood within the passageway 129 and the conduit 112 is allowed to flow into the assembly 127. The volume of the assembly 127 is greater than the combined volumes of passageway 129 and conduit 112, such that assembly 127 contains the mixture of blood and fluid and the passageway 129 contains only blood. The valve assembly 126 is closed to prevent the flow of the mixture of blood and fluid from the assembly 127 into the passageway 129. The extraction device 2 is then brought into contact with the port 122 and the valve assembly 1221 is opened to permit the withdrawal of the blood sample from the second passageway 120.

Once the blood sample has been withdrawn, the flow of fluid through the second passageway 129 can be reinstated. The valve assembly 126 is opened to permit the flow of the blood and fluid mixture in the reservoir assembly 127 into the second passageway 129. The valve assembly 125 is then operated to permit the flow of fluid from the first passageway 128 into the flushing reservoir assembly 127, as shown in FIG. 16. The fluid flows from the first passageway 128 through the flushing reservoir assembly 127 into the second passageway.

When it is desired to administer medication, the valve assembly 126 is closed to prevent the flow of fluid through the second passageway 129, as shown in FIG. 20. Medication M may be administered through port 122 into the second passageway 129.

As shown in FIG. 8, the needle assembly 10 is connected to the mounting assembly 140. The mounting assembly 140 is operatively linked to a control unit 160 through a communication link or tether 150, as shown in FIG. 9.

The mounting assembly 140 provides the interface between the controller/data logger associated with the control unit 160 and the disposable needle 110. Imbedded into the mounting assembly 140 are the actuators for the manipulation of the valves 125 and 126 and the reservoir assembly 127. A detector array (not shown) with required associated circuitry is also embedded into the mounting assembly 140 to create a connection with the sensor connectors 123 and 124. Additionally, the mounting assembly 140 includes circuitry formed therein for interaction with the control unit 160.

The control unit 160 may be a portable handheld unit that may be connected to the patient 1 through a strap or band 161, as shown in FIG. 9. It is also contemplated that the control unit 160 may a larger stationary computer controlled monitoring device, or may be connected into other standard monitoring equipment or by a dedicated hardware device.

The control unit 160 performs numerous functions. For example, the control unit 160 provides a visual indication of bodily functions based on the interpretation of the signals from the sensors located in the staged needle 110. Furthermore, the control unit 160 may store and generate a log of the data collected from the sensors for later analysis. The control unit 160 may operate one or more alarms if predetermined vitals of the patient fall below or above accepted levels. The control unit 160 may further automatically operate the valve assemblies located in the connector assembly 120 and the mounting assembly 140 to automatically perform sensing operations and administer fluids to the patient. The control unit 160 further provides a link to the patient's medical history and other records, either through wireless communications, infrared communications, or physical connection for the transmission of sensor data and archiving of patient history.

Another embodiment of the disposable needle assembly will now be described in connection with FIG. 10. The disposable needle assembly 20 includes an elongated needle 210 having an elongated shaft. Like the staged needle 110, the elongated needle 210 is preferably molded from an elastomertic material whose durometer is chosen just above that of flesh to minimize discomfort to the patient. The elongated needle 210 includes first and second passageways 211 and 212, which are integrally formed therein. The elongated needle 210 has an insertion tip 213 formed in one end thereof. An opposite end of the needle 210 is connected to a connector assembly 120, described above.

Figure 10:
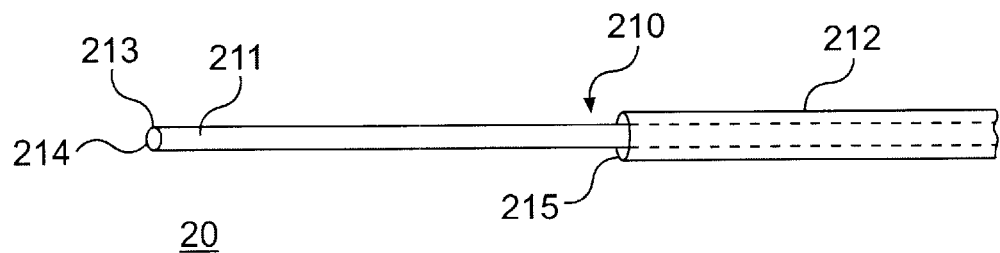
FIG. 10 is a side view of a disposable needle assembly in accordance with another embodiment of the present invention.

The first passageway or conduit 211 extends through the needle 210 from the connector assembly 120 to an opening 214 adjacent the insertion tip 213, as seen in FIG. 10. Like the first conduit 111, the conduit 211 is provided to introduce fluids into the vessel. The second passageway or conduit 212 extends through the elongated needle 210 from the connector assembly 120 to an opening 215 spaced from the insertion tip 213. The second conduit 120 is provided to draw a sample of fluid (e.g. blood) from the vessel. The second conduit 212 extends around the first conduit 211. The differential location of the openings 214 and 215 permits uncontaminated blood draws while simultaneously administering IV fluids. The sensors in assembly 20 are located internally and externally in the second passageway or conduit 212 and internally on conduit 211.

Yet another embodiment of the disposable needle assembly will now be described in connection with FIG. 11. The disposable needle assembly 30 includes an elongated needle 310 having an elongated shaft. Like the needles 110 and 210, the elongated needle 310 is preferably molded from an elastomertic material whose durometer is chosen just above that of flesh to minimize discomfort to the patient. The elongated needle 310 includes first and second passageways 311 and 312, which are integrally formed therein. The elongated needle 310 has an insertion tip 313 formed in one end thereof. An opposite end of the needle 310 is connected to a connector assembly 120, described above.

Figure 11:
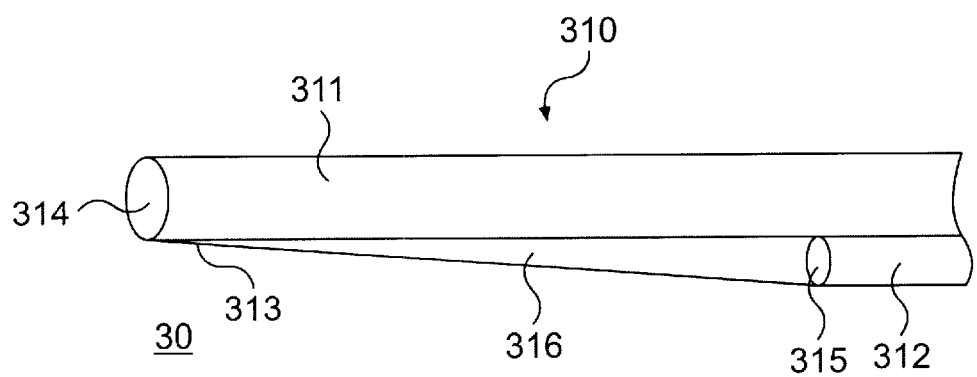
FIG. 11 is a side view of a disposable needle assembly in accordance with yet another embodiment of the present invention.

The first passageway or conduit 311 extends through the needle 310 from the connector assembly 120 to an opening 314 adjacent the insertion tip 313, as seen in FIG. 11. The second passageway or conduit 312 extends through the elongated needle 310 from the connector assembly 120 to an opening 315 spaced from the insertion tip 313. The first and second conduits 311 and 312 are located in a generally side-by-side relationship. A wall 316 extends between the conduits 311 and 312. An end portion of the wall 316 forms the insertion tip 313. The sensors in assembly 30 are located internally and externally in the second passageway or conduit 312 and internally on conduit 311.

Figure 12:
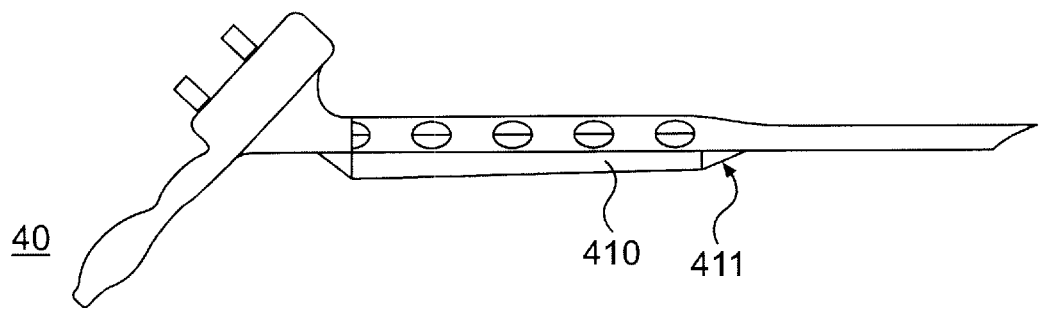
FIG. 12 is a side view of a disposable needle assembly in accordance with still another embodiment of the present invention.

Still another embodiment of the disposable needle assembly will now be described in connection with FIG. 12. The disposable needle assembly 40 has a construction similar to the needle assembly 10. In this arrangement, an additional conduit 410 is provided having a valve assembly 411. The valve assembly 411 permits the sealing off of the conduit at predetermined times in the event of use of medical equipment or drug delivery that may be incompatible with an IV solution. The conduit is contemplated to be "flushed" or swept with the IV or saline solution. The port would delivery all present venous medicinal fluids such as heart medication, chemotherapy drugs, either liquids or solid delivery i.e. capsules.

The manufacture of the elongated shaft of the disposable needle assemblies 10, 20, 30 and 40 will now be described. In accordance with a preferred embodiment of the present invention, the elongated shaft of the disposable needle assembly is formed by micro-injection molding. Micro-injection molding is similar to traditional molding processes in many ways. The molding material is melted in a chamber. An amount of the material is ejected from the chamber through a nozzle into a mold tool. The material moves through a series of channels called runners to reach the void called a cavity, which is the negative of the molded part. The molding material is allowed to cool, creating a solid component. The mold tool opens and the part is ejected from the cavity. The tool closes and the process is repeated.

Micro-injection molding technology offers milligram control on shot size and millisecond control on injection times. In micro-injection molding, the components and runner system are extremely small, only a small amount of material is melted at any one time. In some instances, only a few grams may be melted. Most thermoplastics if held at elevated temperatures for extended periods will degrade and the properties of the final product will be compromised. Furthermore, it is very important that the material does not cool before it is moved in the mold. The precise amount of molding resin is moved into the mold before a cold front is allowed to form on the material. The absence of the cold front allows for better knitting of the material, allows for thinner walls, and greatly reduced molded in stresses.

The formation of the elongated needle 10, 20, 30 and 40 will now be described. In accordance with the present invention, the sensor assemblies 130 and the removable core pin 3 are formed. The sensor assemblies 130 (e.g., the optical sensors) and the core pin 3 may be formed by micro-injection molding. The sensor assemblies 130 and the core pin 3 are located with in the mold for forming the needle shaft. The material forming the needle shaft is then heated and injected into the mold. The material is over molded over the sensor assemblies 130 and the core pin 3. In order to prevent melting of the sensor assemblies 130 and the core pin 3 during the molding of the needle shaft, the materials forming these components must have a melting temperature that is at least 50° F. higher than the melting temperature of the material forming the needle shaft.

The present invention is not limited to the method described above; rather, it is contemplated that other forms of micro-injection molding may be employed. For example, it is contemplated that liquid injection molding may be employed. The component materials forming the needle shaft are mixed and injected into the mold. The mold is then heated to heat the materials. The mold and the needle shaft are then cooled, such that the needle shaft cures.

It will be appreciated that numerous modifications to and departures from the preferred embodiments described above will occur to those having skill in the art. The present invention is not limited to the above-described uses. Thus, it is intended that the present invention covers the modifications and variations of the invention, provided they come within the scope of the appended claims and their equivalents.

What is claimed is:

1. A needle assembly for use in connection with treating a patient for administering fluids to the patient and drawing fluids from the patient, comprising:

an elongated needle shaft having a first end and a second end;

an insertion tip located at a first end of the elongated needle shaft to facilitate insertion of the needle assembly into a vessel of the patient;

at least one fluid drawing passageway formed in the elongated needle shaft for withdrawing fluid from the patient, wherein the at least one fluid drawing passageway extends from the second end of the elongated needle shaft to a fluid drawing opening in the elongated needle shaft, wherein fluid within the vessel is withdrawn through the at least one fluid drawing passageway;

at least one fluid supply passageway formed in the elongated needle shaft for supplying fluid to the patient, wherein the at least one fluid supply passageway extends from the second end of the elongated needle shaft to a fluid supply opening in the elongated needle shaft; and at least one sensor assembly disposed within the elongated needle shaft, wherein the at least one sensor assembly senses at least one predetermined condition of the patient, wherein the at least one sensor assembly includes at least a first sensor operatively connected to the at least one fluid drawing passageway for performing a sensing operation on the fluid within the at least one fluid drawing passageway, wherein the at least a first sensor is located within the at least one fluid drawing passageway, and at least a second sensor for performing a sensing operation on the fluid within the vessel, wherein the at least a second sensor is located at least one of within the at least one fluid supply passageway or on the elongated needle shaft.

2. The needle assembly according to claim 1, wherein one of the fluid supply opening and the fluid drawing opening is located adjacent the insertion tip, wherein the other of the fluid supply opening and the fluid drawing opening is spaced from the insertion tip.

3. The needle assembly according to claim 1, wherein the elongated needle shaft is formed from an elastomeric material, wherein the elastomeric material has a durometer greater than the durometer of flesh.

4. The needle assembly according to claim 1, wherein each of the first sensor and the second sensor is one of a pressure sensor, an optical sensor, a temperature sensor, an acoustic sensor, an electrical sensor and a chemical sensor.

5. A needle assembly for use in connection with treating a patient for administering fluids to the patient and drawing fluids from the patient, comprising:

an elongated needle shaft having a first end and a second end;

an insertion tip located at a first end of the elongated needle shaft to facilitate insertion of the needle assembly into a vessel of the patient;

at least one fluid drawing passageway formed in the elongated needle shaft for withdrawing fluid from the patient, wherein the at least one fluid drawing passageway extends from the second end of the elongated needle shaft to a fluid drawing opening in the elongated needle shaft, wherein fluid within the vessel is withdrawn through the at least one fluid drawing passageway;

at least one fluid supply passageway formed in the elongated needle shaft for supplying fluid to the patient, wherein the at least one fluid supply passageway extends from the second end of the elongated needle shaft to a fluid supply opening in the elongated needle shaft;

at least one sensor assembly disposed within the elongated needle shaft, wherein the at least one sensor assembly senses at least one predetermined condition of the patient; and a connector assembly connected to the second end of the elongated needle shaft, wherein the connector assembly includes at least one inlet port operatively connected to the at least one fluid supply passageway and at least one outlet port operatively connected to the at least one fluid drawing passageway.

6. The needle assembly according to claim 5, further comprising:

an attachment assembly for releasably securing the needle assembly to the patient, wherein the connector assembly is connected to the attachment assembly.

7. The needle assembly according to claim 5, wherein the at least one sensor assembly disposed within the elongated needle shaft comprises:

at least one sensor passageway formed in the elongated needle shaft; and at least one sensor located within the sensor passageway.

8. The needle assembly according to claim 7, wherein the at least one sensor is operatively connected to the at least one fluid drawing passageway for performing a sensing operation on the fluid within the at least one fluid drawing passageway.

9. The needle assembly according to claim 8, wherein the at least one sensor is one of a pressure sensor, an optical sensor, a temperature sensor, an acoustic sensor, an electrical sensor and a chemical sensor.

10. The needle assembly according to claim 7, wherein the at least one sensor assembly performs a sensing operation on the fluid within the vessel.

11. The needle assembly according to claim 10, wherein the at least one sensor is one of a pressure sensor, an optical sensor, a temperature sensor, an acoustic sensor, an electrical sensor and a chemical sensor.

12. The needle assembly according to claim 7, wherein the at least one sensor assembly performs a sensing operation on the patient.

13. The needle assembly according to claim 12, wherein the at least one sensor is one of a pressure sensor, an optical sensor, a temperature sensor, an acoustic sensor, an electrical sensor and a chemical sensor.

14. The needle assembly according to claim 7, wherein the elongated shaft includes at least one recess formed therein, wherein at least a portion of the sensor disposed within the sensor passageway is exposed within the at least one recess formed therein.

15. A needle assembly for use in connection with treating a patient for administering fluids to the patient and drawing fluids from the patient, comprising:

an elongated needle shaft having a first end and a second end;

an insertion tip located at a first end of the elongated needle shaft to facilitate insertion of the needle assembly into a vessel of the patient;

at least one fluid drawing passageway formed in the elongated needle shaft for withdrawing fluid from the patient, wherein the at least one fluid drawing passageway extends from the second end of the elongated needle shaft to a fluid drawing opening in the elongated needle shaft, wherein fluid within the vessel is withdrawn through the at least one fluid drawing passageway;

at least one fluid supply passageway formed in the elongated needle shaft for supplying fluid to the patient, wherein the at least one fluid supply passageway extends from the second end of the elongated needle shaft to a fluid supply opening in the elongated needle shaft;

at least one sensor assembly disposed within the elongated needle shaft, wherein the at least one sensor assembly senses at least one predetermined condition of the patient; and a molded core member removably located within one of the at least one fluid supply passageway and the at least one of the fluid drawing passageway, wherein the molded core member is located within the one passageway during a needle insertion operation.

16. A disposable needle assembly for use in connection with treating a patient, wherein the disposable needle assembly is capable of simultaneously administering fluids to the patient and drawing fluids from the patient, comprising:

an elongated needle shaft having a first end and a second end;

an insertion tip formed in a first end of the elongated needle shaft to facilitate insertion of the needle assembly into a vessel of the patient;

a fluid drawing passageway formed in the elongated needle shaft for withdrawing a first fluid from the patient, wherein the fluid drawing passageway extends from the second end of the elongated needle shaft to a fluid drawing opening in the elongated needle shaft, wherein first fluid within the vessel is withdrawn through the fluid drawing passageway;

a fluid supply passageway formed in the elongated needle shaft for supplying a second fluid to the patient, wherein the fluid supply passageway extends from the second end of the elongated needle shaft to a fluid supply opening in the elongated needle shaft, wherein the fluid drawing opening is spaced from the fluid supply opening to prevent mixing of the first fluid and the second fluid adjacent the fluid drawing opening; and at least one sensor assembly formed within the elongated needle shaft, wherein the at least one sensor assembly senses at least one predetermined condition of the patient, wherein the at least one sensor assembly includes at least a first sensor operatively connected to the at least one fluid drawing passageway for performing a sensing operation on the fluid within the at least one fluid drawing passageway, wherein the at least a first sensor being located within the at least one fluid drawing passageway, and at least a second sensor for performing a sensing operation on the fluid within the vessel, wherein the at least a second sensor is located in at least one of within the at least one fluid supply passageway or on the elongated needle shaft.

17. The needle assembly according to claim 16, wherein the elongated needle shaft is formed from an elastomeric material, wherein the elastomeric material has a durometer greater than the durometer of flesh.

18. The needle assembly according to claim 15, wherein each of the first sensor and the second sensor is one of a pressure sensor, an optical sensor, a temperature sensor, an acoustic sensor, an electrical sensor and a chemical sensor.

19. A disposable needle assembly for use in connection with treating a patient, wherein the disposable needle assembly is capable of simultaneously administering fluids to the patient and drawing fluids from the patient, comprising:

an elongated needle shaft having a first end and a second end;

an insertion tip formed in a first end of the elongated needle shaft to facilitate insertion of the needle assembly into a vessel of the patient;

a fluid drawing passageway formed in the elongated needle shaft for withdrawing a first fluid from the patient, wherein the fluid drawing passageway extends from the second end of the elongated needle shaft to a fluid drawing opening in the elongated needle shaft, wherein first fluid within the vessel is withdrawn through the fluid drawing passageway;

a fluid supply passageway formed in the elongated needle shaft for supplying a second fluid to the patient, wherein the fluid supply passageway extends from the second end of the elongated needle shaft to a fluid supply opening in the elongated needle shaft, wherein the fluid drawing opening is spaced from the fluid supply opening to prevent mixing of the first fluid and the second fluid adjacent the fluid drawing opening;

at least one sensor assembly formed within the elongated needle shaft, wherein the at least one sensor assembly senses at least one predetermined condition of the patient; and a connector assembly connected to the second end of the elongated needle shaft, wherein the connector assembly includes at least one inlet port operatively connected to the at least one fluid supply passageway and at least one outlet port operatively connected to the at least one fluid drawing passageway; and an attachment assembly for releasably securing the needle assembly to the patient, wherein the connector assembly is connected to the attachment assembly.

20. A disposable needle assembly for use in connection with treating a patient, wherein the disposable needle assembly is capable of simultaneously administering fluids to the patient and drawing fluids from the patient, comprising:

an elongated needle shaft having a first end and a second end;

an insertion tip formed in a first end of the elongated needle shaft to facilitate insertion of the needle assembly into a vessel of the patient;

a fluid drawing passageway formed in the elongated needle shaft for withdrawing a first fluid from the patient, wherein the fluid drawing passageway extends from the second end of the elongated needle shaft to a fluid drawing opening in the elongated needle shaft, wherein first fluid within the vessel is withdrawn through the fluid drawing passageway;

a fluid supply passageway formed in the elongated needle shaft for supplying a second fluid to the patient, wherein the fluid supply passageway extends from the second end of the elongated needle shaft to a fluid supply opening in the elongated needle shaft, wherein the fluid drawing opening is spaced from the fluid supply opening to prevent mixing of the first fluid and the second fluid adjacent the fluid drawing opening;

at least one sensor assembly formed within the elongated needle shaft, wherein the at least one sensor assembly senses at least one predetermined condition of the patient; and a pair of sensor passageways formed in the elongated needle shaft, wherein the pair of sensor passageways are formed on opposite sides of at least one of the fluid drawing passageway and the fluid supply passageway; and at least one a sensor located in each sensor passageway.

21. The disposable needle assembly according to claim 20, wherein the sensor is one of an optical sensor, a temperature sensor, an electrical sensor and a chemical sensor.

22. The needle assembly according to claim 20, wherein the elongated shaft includes at least one recess formed therein, wherein at least a portion of the sensor disposed within the sensor passageway is exposed within the at least one recess formed therein.

23. A disposable needle assembly for use in connection with treating a patient, wherein the disposable needle assembly is capable of simultaneously administering fluids to the patient and drawing fluids from the patient, comprising:

an elongated needle shaft having a first end and a second end;

an insertion tip formed in a first end of the elongated needle shaft to facilitate insertion of the needle assembly into a vessel of the patient;

a fluid drawing passageway formed in the elongated needle shaft for withdrawing a first fluid from the patient, wherein the fluid drawing passageway extends from the second end of the elongated needle shaft to a fluid drawing opening in the elongated needle shaft, wherein first fluid within the vessel is withdrawn through the fluid drawing passageway;

a fluid supply passageway formed in the elongated needle shaft for supplying a second fluid to the patient, wherein the fluid supply passageway extends from the second end of the elongated needle shaft to a fluid supply opening in the elongated needle shaft, wherein the fluid drawing opening is spaced from the fluid supply opening to prevent mixing of the first fluid and the second fluid adjacent the fluid drawing opening;

at least one sensor assembly formed within the elongated needle shaft, wherein the at least one sensor assembly senses at least one predetermined condition of the patient; and a molded core member removably located within one of the at least one fluid supply passageway and the at least one of the fluid draw, wherein the molded core member is located within the one passageway during a needle insertion operation.

* * * * *